United States Patent

Takematsu et al.

Patent Number: 4,747,866
Date of Patent: May 31, 1988

[54] PYRIMIDINYLOXYALKANAMIDE DERIVATIVES AND HERBICIDE COMPOSITION CONTAINING THE SAME

[75] Inventors: Tetsuo Takematsu; Yasutomo Takeuchi, both of Utsunomiya; Mitsuaki Takenaka, Ube; Seiji Takamura, Ube; Hiroshi Hase, Ube, all of Japan

[73] Assignee: Ube Industries, Ltd., Ube, Japan

[21] Appl. No.: 897,306

[22] Filed: Aug. 15, 1986

[30] Foreign Application Priority Data

Aug. 20, 1985 [JP] Japan .................. 60-180987

[51] Int. Cl.$^4$ .................. A61K 31/34; A61K 31/505
[52] U.S. Cl. .................. 71/92; 544/301; 544/302; 544/310; 544/312; 544/313; 544/314; 544/319; 544/320; 544/321; 71/90
[58] Field of Search ........... 544/301, 302, 310, 312, 544/313, 314, 319, 320, 321; 71/90, 92

[56] References Cited

U.S. PATENT DOCUMENTS 4,517,188 5/1985 Lawson et al. ................ 544/319

Primary Examiner—Henry R. Jiles
Assistant Examiner—J. G. Mullins
Attorney, Agent, or Firm—Frishauf, Holtz, Goodman & Woodward

[57] ABSTRACT

A pirimidinyloxyalkanamide derivative of Formula 1:

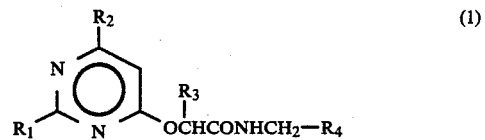

wherein $R_1$ represents a hydrogen atom, a halogen atom, a lower alkyl group, a lower alkylthio group, a lower alkenylthio group, a lower alkynylthio group, a halogenated lower alkenylthio group, a cycloalkylthio group, an aroxyalkylthio group, a lower alkoxyl group, an amino group, a methanesulfonyl group, a trifluoromethyl group, an anilino group which may be substituted with a halogen atom or a benzylthio group which may be substituted with a halogen atom; $R_2$ represents a hydrogen atom, a halogen atom, a lower alkyl group, a trifluoromethyl group, an amino group, a lower alkoxy group or a lower alkylthio group; $R_3$ represents an ethyl group or an n-propyl group; and $R_4$ represents a cyclohexyl group, a thienyl group, a pyridyl group, a furyl group or a

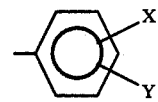

group wherein X and Y may be the same or different and each represent a hydrogen atom, a lower alkyl group, a trifluoromethyl group, a lower alkoxyl group or a halogen atom, and a herbicide composition comprising the same as an active ingredient.

13 Claims, No Drawings

PYRIMIDINYLOXYALKANAMIDE DERIVATIVES AND HERBICIDE COMPOSITION CONTAINING THE SAME

BACKGROUND OF THE INVENTION

The present invention relates to a pyrimidinyloxyalkanamide derivative and a herbicide composition comprising the same as an active ingredient.

More particulary, the present invention relates to a pirimidinyloxyalkanamide derivative of Formula 1:

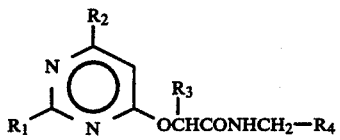
(1)

wherein $R_1$ represents a hydrogen atom, a halogen atom, a lower alkyl group, a lower alkylthio group, a lower alkenylthio group, a lower alkynylthio group, a halogenated lower alkenylthio group, a cycloalkylthio group, an aroxyalkylthio group, a lower alkoxyl group, an amino group, a methanesulfonyl group, a trifluoromethyl group, an anilino group which may be substituted with a halogen atom or a benzylthio group which may be substituted with a halogen atom; $R_2$ represents a hydrogen atom, a halogen atom, a lower alkyl group, a trifluoromethyl group, an amino group, a lower alkoxyl group or a lower alkylthio group; $R_3$ represents an ethyl group or an n-propyl group; and $R_4$ represents a cyclohexyl group, a thienyl group, a pyridyl group, a furyl group or a

group wherein X and Y may be the same or different and each represent a hydrogen atom, a lower alkyl group, a trifluoromethyl group, a lower alkoxyl group or a halogen atom,
and a herbicide composition comprising the same as an active ingredient.

In agricultural production, weeds may cause various problems such as decrease in harvest yield, as well as, deterioration in quality of products, decreased efficiency in harvesting operation, etc. As a means to inhibit growth of weeds or to kill them at a fairly low cost, herbicides have recently been developed, however, there still remain some unsolved problems.

Thus, it has been earnestly desired to develope such herbicides that can exhibit stable herbicidal activity without giving any deleterious effect of chemical on crops under any environmental conditions including temperature, soil condition, etc., that can exhibit activity to a wide range of grasses (Gramineae) and broad leaf weeds and that are active to the weeds which conventional herbicides failed to kill, such as velvetleaf (*Abutilon theophrasti*), prickly sida (*Sida spinosa*), *Cassia tora*, common morningglory (*Ipomoea purpurea*), etc.

The present inventors have made extensive studies to overcome such problems, and as a result, found that a pirimidinyloxyalkanamide derivative of Formula I exhibits herbicidal effect widely on both of grasses (Gramineal) such as large crabgrass (*Digitaria sanguinalis*), barnyardgrass (*Echinochloa crusgalli*), etc. and broad leaf weeds such as common purslane (*Portulaca oleracea*), redroot pigweed (*Amaranthus retroflexus*) and common lambsquarters (*Chenopodium album*), and also high herbicidal activity on weeds which are difficult to be controlled by conventional herbicides, such as *Abutilon theophrasti*, *Sida spinosa*, *Cassia tora* and *Ipomoea purpurea*, without giving any adverse effect of chemical on various crops such as a paddy-rice seedling, wheat (*Triticum aestivum*, cotton (*Gossypium hirusutum*), soybean (*Glycine max*), sorghum (*Sorghum bicolor*), tomato (*Lycopersicum esculentum*), etc., accomplishing the present invention.

As patents related to the present invention, there may be mentioned Japanese Unexamined Patent Publication Nos. 67653/1983, 113155/1983, 113156/1983 and 29645/1984, disclosing a series of phenoxyalkanoic acid amide derivatives.

SUMMARY OF THE INVENTION

Namely, the present invention is directed to provide a pirimidinyloxyalkanamide derivative of Formula 1:

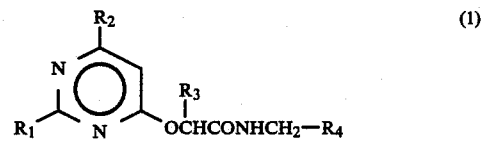
(1)

wherein $R_1$ represents a hydrogen atom, a halogen atom, a lower alkyl group, a lower alkylthio group, a lower alkenylthio group, a lower alkynylthio group, a halogenated lower alkenylthio group, a cycloalkylthio group, an aroxyalkylthio group, a lower alkoxyl group, an amino group, a methanesulfonyl group, a trifluoromethyl group, an anilino group which may be substituted with a halogen atom or a benzylthio group which may be substituted with a halogen atom; $R_2$ represents a hydrogen atom, a halogen atom, a lower alkyl group, a trifluoromethyl group, an amino group, a lower alkoxyl group or a lower alkylthio group; $R_3$ represents an ethyl group or an n-propyl group; and $R_4$ represents a cyclohexyl group, a thienyl group, a pyridyl group, a furyl group or a

group wherein X and Y may be the same or different and each represent a hydrogen atom, a lower alkyl group, a trifluoromethyl group, a lower alkoxyl group or a halogen atom,
and a herbicide composition comprising the same as an active ingredient.

DETAILED DESCRIPTION OF THE PREFERRED EMBODIMENTS

Specific examples of the pirimidinyloxyalkanamide derivatives of the above Formula 1 of the present invention are listed in Table 1.

TABLE 1

| Compound No. | Formula | Physical property | Yield (%) | State |
|---|---|---|---|---|
| 1 | CH₃S-pyrimidine(CH₃)-O-CH(C₂H₅)-CONHCH₂-cyclohexyl | m.p. 118~119° C. | 83 | Colorless needle |
| 2 | (CH₃)₃C-S-pyrimidine(CH₃)-O-CH(C₂H₅)-CONHCH₂-cyclohexyl | m.p. 88~89° C. | 55 | Colorless prism |
| 3 | CH₃S-pyrimidine(CH₃)-O-CH(C₂H₅)-CONHCH₂-phenyl | m.p. 162~163° C. | 77 | " |
| 4 | CH₃S-pyrimidine(CH₃)-O-CH(C₂H₅)-CONHCH₂-(2-CH₃-phenyl) | m.p. 149~150° C. | 78 | Colorless needle |
| 5 | CH₃S-pyrimidine(CH₃)-O-CH(C₂H₅)-CONHCH₂-(3-CH₃-phenyl) | m.p. 111~112° C. | 55 | " |
| 6 | CH₃S-pyrimidine(CH₃)-O-CH(C₂H₅)-CONHCH₂-(4-CH₃-phenyl) | m.p. 130~131° C. | 62 | " |
| 7 | CH₃S-pyrimidine(CH₃)-O-CH(C₂H₅)-CONHCH₂-(2-CH₃O-phenyl) | m.p. 122~123° C. | 75 | " |
| 8 | CH₃S-pyrimidine(CH₃)-O-CH(C₂H₅)-CONHCH₂-(3-OCH₃-phenyl) | m.p. 114~115° C. | 68 | " |

TABLE 1-continued

| Compound No. | Formula | Physical property | Yield (%) | State |
|---|---|---|---|---|
| 9 | CH₃S-pyrimidine(CH₃)-OCH(C₂H₅)CONHCH₂-C₆H₄-OCH₃ | m.p. 109~110° C. | 54 | " |
| 10 | CH₃S-pyrimidine(CH₃)-OCH(C₂H₅)CONHCH₂-C₆H₃(CH₃)₂ | m.p. 147~148° C. | 67 | " |
| 11 | CH₃S-pyrimidine(CH₃)-OCH(C₂H₅)CONHCH₂-C₆H₄-F (o-F) | m.p. 119~122° C. | 54 | " |
| 12 | CH₃S-pyrimidine(CH₃)-OCH(C₂H₅)CONHCH₂-C₆H₄-F (m-F) | m.p. 107~110° C. | 23 | " |
| 13 | CH₃S-pyrimidine(CH₃)-OCH(C₂H₅)CONHCH₂-C₆H₄-F (p-F) | m.p. 119~120° C. | 38 | Colorless prism |
| 14 | CH₃S-pyrimidine(CH₃)-OCH(C₂H₅)CONHCH₂-C₆H₄-Cl (o-Cl) | m.p. 110~117° C. | 47 | Colorless needle |
| 15 | CH₃S-pyrimidine(CH₃)-OCH(C₂H₅)CONHCH₂-C₆H₄-Cl (m-Cl) | m.p. 115~116° C. | 53 | " |
| 16 | CH₃S-pyrimidine(CH₃)-OCH(C₂H₅)CONHCH₂-C₆H₄-Cl (p-Cl) | m.p. 134~135° C. | 65 | " |

TABLE 1-continued

| Compound No. | Formula | Physical property | Yield (%) | State |
|---|---|---|---|---|
| 17 | 4-(CH₃), 2-(CH₃S)-pyrimidin-6-yl —OCH(C₂H₅)CONHCH₂—(2,3-dichlorophenyl) | m.p. 134~135° C. | 75 | " |
| 18 | 4-(CH₃), 2-(CH₃S)-pyrimidin-6-yl —OCH(C₂H₅)CONHCH₂—(2,5-dichlorophenyl) | m.p. 114~115° C. | 47 | " |
| 19 | 4-(CH₃), 2-(CH₃S)-pyrimidin-6-yl —OCH(C₂H₅)CONHCH₂—(2,6-dichlorophenyl) | m.p. 169~170° C. | 62 | " |
| 20 | 4-(CH₃), 2-(CH₃S)-pyrimidin-6-yl —OCH(C₂H₅)CONHCH₂—(2-bromophenyl) | m.p. 114~115° C. | 52 | " |
| 21 | 4-(CH₃), 2-(CH₃S)-pyrimidin-6-yl —OCH(C₂H₅)CONHCH₂—(4-bromophenyl) | m.p. 138~139° C. | 37 | " |
| 22 | 4-(CH₃), 2-(CH₃S)-pyrimidin-6-yl —OCH(C₂H₅)CONHCH₂—(2-trifluoromethylphenyl) | m.p. 123~124° C. | 47 | " |
| 23 | 4-(CH₃), 2-(CH₃S)-pyrimidin-6-yl —OCH(C₂H₅)CONHCH₂—(3-trifluoromethylphenyl) | m.p. 115~116° C. | 28 | " |
| 24 | 4-(CH₃), 2-(CH₃S)-pyrimidin-6-yl —OCH(C₂H₅)CONHCH₂—(furan-2-yl) | m.p. 121~122° C. | 38 | " |

TABLE 1-continued

| Compound No. | Formula | Physical property | Yield (%) | State |
|---|---|---|---|---|
| 25 | CH₃S-, CH₃-, C₂H₅, pyrimidine-OCHCONHCH₂-thiophene | m.p. 122~123° C. | 55 | " |
| 26 | CH₃S-, CH₃-, C₂H₅, pyrimidine-OCHCONHCH₂-pyridine | m.p. 114~115° C. | 57 | " |
| 27 | C₂H₅S-, CH₃-, C₂H₅, pyrimidine-OCHCONHCH₂-phenyl | m.p. 111~112° C. | 57 | " |
| 28 | C₂H₅S-, CH₃-, C₂H₅, pyrimidine-OCHCONHCH₂-(2-CH₃-phenyl) | m.p. 111~112° C. | 52 | " |
| 29 | C₂H₅S-, CH₃-, C₂H₅, pyrimidine-OCHCONHCH₂-(3-CH₃-phenyl) | m.p. 83~84° C. | 48 | " |
| 30 | C₂H₅S-, CH₃-, C₂H₅, pyrimidine-OCHCONHCH₂-(2-CH₃O-phenyl) | m.p. 94~95° C. | 68 | " |
| 31 | C₂H₅S-, CH₃-, C₂H₅, pyrimidine-OCHCONHCH₂-(3-OCH₃-phenyl) | m.p. 103~104° C. | 74 | " |
| 32 | C₂H₅S-, CH₃-, C₂H₅, pyrimidine-OCHCONHCH₂-(2-Cl-phenyl) | m.p. 108~109° C. | 72 | " |
| 33 | C₂H₅S-, CH₃-, C₂H₅, pyrimidine-OCHCONHCH₂-(3-Cl-phenyl) | m.p. 82~83° C. | 62 | " |

TABLE 1-continued

| Compound No. | Formula | Physical property | Yield (%) | State |
|---|---|---|---|---|
| 34 | C₂H₅S—[pyrimidine(CH₃)]—OCH(C₂H₅)CONHCH₂—[2,4-dichlorophenyl] | m.p. 112~114° C. | 72 | " |
| 35 | C₂H₅S—[pyrimidine(CH₃)]—OCH(C₂H₅)CONHCH₂—[bromophenyl] | m.p. 108~112° C. | 33 | " |
| 36 | C₂H₅S—[pyrimidine(CH₃)]—OCH(C₂H₅)CONHCH₂—[thienyl] | m.p. 107~108° C. | 30 | " |
| 37 | C₂H₅S—[pyrimidine(CH₃)]—OCH(C₂H₅)CONHCH₂—[pyridyl] | m.p. 109~110° C. | 63 | " |
| 38 | n-C₃H₇S—[pyrimidine(CH₃)]—OCH(C₂H₅)CONHCH₂—[phenyl] | m.p. 98~99° C. | 50 | " |
| 39 | n-C₃H₇S—[pyrimidine(CH₃)]—OCH(C₂H₅)CONHCH₂—[tolyl] | m.p. 121~122° C. | 70 | " |
| 40 | n-C₃H₇S—[pyrimidine(CH₃)]—OCH(C₂H₅)CONHCH₂—[tolyl] | m.p. 83~84° C. | 30 | " |
| 41 | n-C₃H₇S—[pyrimidine(CH₃)]—OCH(C₂H₅)CONHCH₂—[chlorophenyl] | m.p. 111~113° C. | 75 | " |

TABLE 1-continued

| Compound No. | Formula | Physical property | Yield (%) | State |
|---|---|---|---|---|
| 42 | CH₃, n-C₃H₇S-pyrimidine-OCH(C₂H₅)CONHCH₂-(3-Cl-phenyl) | m.p. 88~89° C. | 52 | " |
| 43 | CH₃, n-C₃H₇S-pyrimidine-OCH(C₂H₅)CONHCH₂-(4-Br-phenyl) | m.p. 108~109° C. | 83 | " |
| 44 | CH₃, n-C₃H₇S-pyrimidine-OCH(C₂H₅)CONHCH₂-(2-thienyl) | m.p. 85~86° C. | 58 | " |
| 45 | CH₃, i-C₃H₇S-pyrimidine-OCH(C₂H₅)CONHCH₂-phenyl | m.p. 68~69° C. | 47 | " |
| 46 | CH₃, i-C₃H₇S-pyrimidine-OCH(C₂H₅)CONHCH₂-(2-CH₃-phenyl) | $n_D^{28.8}$ 1.5534 | 38 | Yellow oil |
| 47 | CH₃, CH₂=CHCH₂S-pyrimidine-OCH(C₂H₅)CONHCH₂-phenyl | m.p. 91~92° C. | 50 | Colorless needle |
| 48 | CH₃, CH₂=CHCH₂S-pyrimidine-OCH(C₂H₅)CONHCH₂-(2-CH₃-phenyl) | m.p. 111~112° C. | 52 | " |
| 49 | CH₃, CH₂=CHCH₂S-pyrimidine-OCH(C₂H₅)CONHCH₂-(2-Cl-phenyl) | m.p. 150~151° C. | 42 | " |
| 50 | CH₃, CH₂=CHCH₂S-pyrimidine-OCH(C₂H₅)CONHCH₂-(3-Cl-phenyl) | m.p. 82~83° C. | 62 | " |

TABLE 1-continued

| Compound No. | Formula | Physical property | Yield (%) | State |
|---|---|---|---|---|
| 51 | CH₂=CHCH₂S–[pyrimidine(CH₃,N,N)]–OCH(C₂H₅)CONHCH₂–[thiophene-S] | $n_D^{24.8}$ 1.5119 | 58 | Colorless oil |
| 52 | CH₂=C(Cl)CH₂S–[pyrimidine(CH₃,N,N)]–OCH(C₂H₅)CONHCH₂–[phenyl] | m.p. 95~97° C. | 6.4 | Colorless needle |
| 53 | CH≡CCH₂S–[pyrimidine(CH₃,N,N)]–OCH(C₂H₅)CONHCH₂–[phenyl] | m.p. 111~112° C. | 15 | " |
| 54 | CH≡CCH₂S–[pyrimidine(CH₃,N,N)]–OCH(C₂H₅)CONHCH₂–[phenyl-CH₃] | m.p. 137~138° C. | 37 | " |
| 55 | CH≡CCH₂S–[pyrimidine(CH₃,N,N)]–OCH(C₂H₅)CONHCH₂–[phenyl-Cl] | m.p. 125~127° C. | 47 | " |
| 56 | n-C₄H₉S–[pyrimidine(CH₃,N,N)]–OCH(C₂H₅)CONHCH₂–[phenyl] | m.p. 83~84° C. | 57 | " |
| 57 | n-C₄H₉S–[pyrimidine(CH₃,N,N)]–OCH(C₂H₅)CONHCH₂–[phenyl-CH₃] | m.p. 100~101° C. | 50 | " |
| 58 | n-C₄H₉S–[pyrimidine(CH₃,N,N)]–OCH(C₂H₅)CONHCH₂–[phenyl-CH₃] | m.p. 62~65° C. | 22 | " |

TABLE 1-continued

| Compound No. | Formula | Physical property | Yield (%) | State |
|---|---|---|---|---|
| 59 | n-C$_4$H$_9$S—[pyrimidine(CH$_3$, OCH(C$_2$H$_5$)CONHCH$_2$-)]—C$_6$H$_4$-Cl | m.p. 95~96° C. | 80 | " |
| 60 | t-C$_4$H$_9$S—[pyrimidine(CH$_3$, OCH(C$_2$H$_5$)CONHCH$_2$-)]—C$_6$H$_5$ | $n_D^{27.5}$ 1.5552 | 40 | Colorless oil |
| 61 | t-C$_4$H$_9$S—[pyrimidine(CH$_3$, OCH(C$_2$H$_5$)CONHCH$_2$-)]—C$_6$H$_4$-CH$_3$ | $n_D^{28.2}$ 1.5523 | 63 | Yellow oil |
| 62 | t-C$_4$H$_9$S—[pyrimidine(CH$_3$, OCH(C$_2$H$_5$)CONHCH$_2$-)]—C$_6$H$_4$-Cl | m.p. 114~117° C. | 60 | Colorless needle |
| 63 | t-C$_4$H$_9$S—[pyrimidine(CH$_3$, OCH(C$_2$H$_5$)CONHCH$_2$-)]—C$_6$H$_4$-Br | m.p. 104~106° C. | 50 | Colorless plate |
| 64 | t-C$_4$H$_9$S—[pyrimidine(CH$_3$, OCH(C$_2$H$_5$)CONHCH$_2$-)]—C$_6$H$_4$-CF$_3$ | $n_D^{12.2}$ 1.5328 | 67 | Colorless oil |
| 65 | CH$_2$=C(CH$_3$)CH$_2$S—[pyrimidine(CH$_3$, OCH(C$_2$H$_5$)CONHCH$_2$-)]—C$_6$H$_5$ | m.p. 77~78° C. | 23 | Colorless prism |
| 66 | CH$_2$=C(CH$_3$)CH$_2$S—[pyrimidine(CH$_3$, OCH(C$_2$H$_5$)CONHCH$_2$-)]—C$_6$H$_4$-CH$_3$ | m.p. 82~84° C. | 86 | Colorless needle |

TABLE 1-continued

| Compound No. | Formula | Physical property | Yield (%) | State |
|---|---|---|---|---|
| 67 | CH₂=CCH₂S-[pyridine(CH₃, N)]-OCHCONHCH₂-[C₆H₄-Cl], with CH₃ on CH₂=C, C₂H₅ on OCH | m.p. 95~96° C. | 43 | Colorless prism |
| 68 | CH₃CH=CHCH₂S-[pyridine(CH₃)]-OCH(C₂H₅)CONHCH₂-[C₆H₅] | m.p. 89~91° C. | 13 | Colorless needle |
| 69 | n-C₅H₁₁S-[pyridine(CH₃)]-OCH(C₂H₅)CONHCH₂-[C₆H₅] | m.p. 80~82° C. | 49 | " |
| 70 | n-C₅H₁₁S-[pyridine(CH₃)]-OCH(C₂H₅)CONHCH₂-[C₆H₄-CH₃] | m.p. 90~92° C. | 46 | " |
| 71 | n-C₅H₁₁S-[pyridine(CH₃)]-OCH(C₂H₅)CONHCH₂-[C₆H₄-Cl] | m.p. 83~85° C. | 37 | " |
| 72 | i-C₅H₁₁S-[pyridine(CH₃)]-OCH(C₂H₅)CONHCH₂-[C₆H₅] | m.p. 60~61° C. | 65 | " |
| 73 | i-C₅H₁₁S-[pyridine(CH₃)]-OCH(C₂H₅)CONHCH₂-[C₆H₄-CH₃] | m.p. 73~74° C. | 55 | " |
| 74 | i-C₅H₁₁S-[pyridine(CH₃)]-OCH(C₂H₅)CONHCH₂-[C₆H₄-Cl] | m.p. 73~74° C. | 68 | " |

TABLE 1-continued

| Compound No. | Formula | Physical property | Yield (%) | State |
|---|---|---|---|---|
| 75 | (2-ethylbutan-2-ylthio)-4-methyl-6-[1-ethoxy-N-(2-methylbenzyl)acetamido]pyrimidine | $n_D^{22.4}$ 1.5564 | 31 | Yellow oil |
| 76 | (2-ethylbutan-2-ylthio)-4-methyl-6-[1-ethoxy-N-(2-chlorobenzyl)acetamido]pyrimidine | m.p. 104~106° C. | 44 | Colorless needle |
| 77 | 2-cyclopentylthio-4-methyl-6-[1-ethoxy-N-benzylacetamido]pyrimidine | $n_D^{22}$ 1.5681 | 57 | Colorless oil |
| 78 | 2-cyclopentylthio-4-methyl-6-[1-ethoxy-N-(2-methylbenzyl)acetamido]pyrimidine | $n_D^{22}$ 1.5702 | 75 | " |
| 79 | 2-cyclopentylthio-4-methyl-6-[1-ethoxy-N-(2-chlorobenzyl)acetamido]pyrimidine | $n_D^{22}$ 1.5737 | 90 | " |
| 80 | 2-n-hexylthio-4-methyl-6-[1-ethoxy-N-benzylacetamido]pyrimidine | m.p. 86~87° C. | 30 | Colorless needle |
| 81 | 2-n-hexylthio-4-methyl-6-[1-ethoxy-N-(2-methylbenzyl)acetamido]pyrimidine | m.p. 83~85° C. | 27 | " |
| 82 | 2-n-hexylthio-4-methyl-6-[1-ethoxy-N-(2-chlorobenzyl)acetamido]pyrimidine | m.p. 87° C. | 35 | " |

TABLE 1-continued

| Compound No. | Formula | Physical property | Yield (%) | State |
|---|---|---|---|---|
| 83 | n-C₇H₁₅S-[pyrimidine(CH₃, C₂H₅)]-OCHCONHCH₂-phenyl | m.p. 84~85° C. | 36 | " |
| 84 | n-C₈H₁₇S-[pyrimidine(CH₃)]-OCHCONHCH₂-phenyl | m.p. 60~63° C. | 31 | " |
| 85 | phenyl-CH₂S-[pyrimidine(CH₃, C₂H₅)]-OCHCONHCH₂-phenyl | m.p. 118~120° C. | 47 | " |
| 86 | Cl-phenyl-CH₂S-[pyrimidine(CH₃, C₂H₅)]-OCHCONHCH₂-phenyl | m.p. 121~123° C. | 55 | Colorless prism |
| 87 | phenyl-OCH₂CH₂S-[pyrimidine(CH₃, C₂H₅)]-OCHCONHCH₂-phenyl | m.p. 115~120° C. | 61 | Colorless needle |
| 88 | CH₃S-[pyrimidine(CH₃, C₃H₇-n)]-OCHCONHCH₂-phenyl | m.p. 110~111° C. | 43 | " |
| 89 | CH₃S-[pyrimidine(CH₃, C₃H₇-n)]-OCHCONHCH₂-phenyl(CH₃) | m.p. 133~134° C. | 62 | " |
| 90 | CH₃S-[pyrimidine(CH₃, C₃H₇-n)]-OCHCONHCH₂-phenyl | m.p. 109~111° C. | 51 | " |

TABLE 1-continued

| Compound No. | Formula | Physical property | Yield (%) | State |
|---|---|---|---|---|
| 91 | C2H5S—[pyrimidine(CH3, N, N)]—O-CH(C3H7-n)-CONHCH2—[phenyl] | m.p. 86~87° C. | 86 | " |
| 92 | C2H5S—[pyrimidine(CH3, N, N)]—O-CH(C3H7-n)-CONHCH2—[phenyl-Cl] | m.p. 112~114° C. | 45 | " |
| 93 | CH2=CHCH2S—[pyrimidine(CH3, N, N)]—O-CH(C3H7-n)-CONHCH2—[phenyl] | m.p. 78~79° C. | 72 | " |
| 94 | CH2=CHCH2S—[pyrimidine(CH3, N, N)]—O-CH(C3H7-n)-CONHCH2—[phenyl-Cl] | m.p. 103~105° C. | 55 | " |
| 95 | CH3—[pyrimidine(CH3, N, N)]—O-CH(C2H5)-CONHCH2—[phenyl] | m.p. 117~118° C. | 53 | " |
| 96 | CH3—[pyrimidine(CH3, N, N)]—O-CH(C2H5)-CONHCH2—[phenyl-CH3] | m.p. 156~157° C. | 58 | " |
| 97 | n-C3H7—[pyrimidine(CH3, N, N)]—O-CH(C2H5)-CONHCH2—[phenyl] | m.p. 71~72° C. | 17 | Pale yellow needle |
| 98 | n-C3H7—[pyrimidine(CH3, N, N)]—O-CH(C2H5)-CONHCH2—[phenyl-CH3] | m.p. 89~90° C. | 60 | Colorless needle |

TABLE 1-continued

| Compound No. | Formula | Physical property | Yield (%) | State |
|---|---|---|---|---|
| 99 | n-C3H7-[pyrimidine(CH3)]-OCH(C2H5)CONHCH2-[C6H4-Cl] | m.p. 74~76° C. | 66 | " |
| 100 | i-C3H7-[pyrimidine(CH3)]-OCH(C2H5)CONHCH2-[C6H5] | m.p. 98~99° C. | 52 | " |
| 101 | i-C3H7-[pyrimidine(CH3)]-OCH(C2H5)CONHCH2-[C6H4-CH3] | m.p. 106~107° C. | 71 | " |
| 102 | i-C3H7-[pyrimidine(CH3)]-OCH(C2H5)CONHCH2-[C6H4-Cl] | m.p. 106~107° C. | 57 | " |
| 103 | n-C4H9-[pyrimidine(CH3)]-OCH(C2H5)CONHCH2-[C6H5] | m.p. 76~77° C. | 20 | " |
| 104 | n-C4H9-[pyrimidine(CH3)]-OCH(C2H5)CONHCH2-[C6H4-CH3] | m.p. 88~91° C. | 23 | Pale Yellow needle |
| 105 | t-C4H9-[pyrimidine(CH3)]-OCH(C2H5)CONHCH2-[C6H5] | m.p. 90~91° C. | 83 | Colorless needle |
| 106 | CH3O-[pyrimidine(CH3)]-OCH(C2H5)CONHCH2-[C6H5] | m.p. 83~86° C. | 11 | " |

TABLE 1-continued

| Compound No. | Formula | Physical property | Yield (%) | State |
|---|---|---|---|---|
| 107 | 6-methyl-2-amino-pyrimidin-4-yl O-CH(C₂H₅)-CONH-CH₂-phenyl | m.p. 177~180° C. | 13 | Colorless prism |
| 108 | 6-methyl-2-(phenylamino)-pyrimidin-4-yl O-CH(C₂H₅)-CONH-CH₂-phenyl | m.p. 180~181° C. | 42 | Colorless needle |
| 109 | 6-methyl-2-(2-chlorophenylamino)-pyrimidin-4-yl O-CH(C₂H₅)-CONH-CH₂-phenyl | m.p. 182~183° C. | 68 | " |
| 110 | 6-methyl-2-chloro-pyrimidin-4-yl O-CH(C₂H₅)-CONH-CH₂-phenyl | m.p. 109~110° C. | 19 | " |
| 111 | 6-methyl-2-chloro-pyrimidin-4-yl O-CH(C₂H₅)-CONH-CH₂-(4-methylphenyl) | m.p. 133~135° C. | 64 | " |
| 112 | 6-methyl-2-chloro-pyrimidin-4-yl O-CH(C₂H₅)-CONH-CH₂-(2-chlorophenyl) | m.p. 123~124° C. | 35 | " |
| 113 | 2,6-dimethyl-pyrimidin-4-yl O-CH(n-C₃H₇)-CONH-CH₂-phenyl | m.p. 145~146° C. | 62 | " |
| 114 | 6-methyl-2-(n-C₃H₇)-pyrimidin-4-yl O-CH(n-C₃H₇)-CONH-CH₂-(chlorophenyl) | m.p. 65~69° C. | 8 | " |

TABLE 1-continued

| Compound No. | Formula | Physical property | Yield (%) | State |
|---|---|---|---|---|
| 115 | 5-Cl, 2-(OCH(C₂H₅)CONHCH₂-C₆H₅) pyridine | m.p. 146~148° C. | 56 | " |
| 116 | 6-(CH₃S), 2-(OCH(C₂H₅)CONHCH₂-C₆H₅) pyridine | m.p. 112~113° C. | 13 | " |
| 117 | 6-(C₂H₅S), 2-(OCH(C₂H₅)CONHCH₂-C₆H₅) pyridine | m.p. 91~92° C. | 32 | Colorless prism |
| 118 | 6-(n-C₃H₇S), 2-(OCH(C₂H₅)CONHCH₂-C₆H₅) pyridine | m.p. 61~62° C. | 10 | Colorless needle |
| 119 | 5-(S-C₂H₅), 2-(OCH(C₂H₅)CONHCH₂-(2-Cl-C₆H₄)) pyridine | m.p. 82~85° C. | 46 | " |
| 120 | 5-(S-C₄H₉-t), 2-(OCH(C₂H₅)CONHCH₂-C₆H₅) pyridine | m.p. 140~141° C. | 28 | Colorless crystal |
| 121 | 5-(S-C₄H₉-t), 2-(OCH(C₂H₅)CONHCH₂-(2-Cl-C₆H₄)) pyridine | m.p. 139~141° C. | 52 | Colorless crystal |
| 122 | 5-(C₃H₇-n), 6-(CH₃S), 2-(OCH(C₂H₅)CONHCH₂-C₆H₅) pyridine | m.p. 102~103° C. | 20 | Colorless needle |
| 123 | 5-(CF₃), 6-(CH₃S), 2-(OCH(C₂H₅)CONHCH₂-C₆H₅) pyridine | m.p. 111~112° C. | 32 | " |

TABLE 1-continued

| Compound No. | Formula | Physical property | Yield (%) | State |
|---|---|---|---|---|
| 124 | CF₃ / CH₃S-pyrimidine-OCH(C₂H₅)CONHCH₂-C₆H₄-Cl | m.p. 132~133° C. | 44 | " |
| 125 | CF₃ / CH₃S-pyrimidine-OCH(C₂H₅)CONHCH₂-C₆H₅ | m.p. 109~111° C. | 55 | " |
| 126 | Cl / t-C₄H₉S-pyrimidine-OCH(C₂H₅)CONHCH₂-C₆H₄-CH₃ | $n_D^{20.4}$ 1.5643 | 35 | Colorless oil |
| 127 | NH₂ / CH₃S-pyrimidine-OCH(C₂H₅)CONHCH₂-C₆H₅ | m.p. 145~147° C. | 10 | Colorless needle |
| 128 | OCH₃ / CH₃O-pyrimidine-OCH(C₂H₅)CONHCH₂-C₆H₅ | m.p. 109~111° C. | 15 | " |
| 129 | C₃H₇-n / CH₃-pyridine-OCH(C₂H₅)CONHCH₂-C₆H₅ | m.p. 106~107° C. | 40 | " |
| 130 | Cl-pyrimidine-OCH(C₂H₅)CONHCH₂-C₆H₅ | m.p. 134~135° C. | 31 | " |
| 131 | Cl-pyrimidine-OCH(C₂H₅)CONHCH₂-C₆H₄-CH₃ | m.p. 108~110° C. | 47 | " |
| 132 | Cl-pyrimidine-OCH(C₂H₅)CONHCH₂-C₆H₄-Cl | m.p. 138~140° C. | 50 | " |

TABLE 1-continued

| Compound No. | Formula | Physical property | Yield (%) | State |
|---|---|---|---|---|
| 133 | 5-Cl-pyridin-2-yl-O-CH(C₂H₅)-CONH-CH₂-(2,3-dimethylphenyl) | m.p. 148~150° C. | 69 | " |
| 134 | 5-Cl-pyridin-2-yl-O-CH(C₂H₅)-CONH-CH₂-phenyl | m.p. 143~145° C. | 58 | " |
| 135 | 5-Cl-pyridin-2-yl-O-CH(C₂H₅)-CONH-CH₂-(4-methylphenyl) | m.p. 165~167° C. | 57 | " |
| 136 | 5-Cl-pyridin-2-yl-O-CH(C₂H₅)-CONH-CH₂-(3-methylphenyl) | m.p. 122~124° C. | 16 | " |
| 137 | 5-Cl-pyridin-2-yl-O-CH(C₂H₅)-CONH-CH₂-(2-chlorophenyl) | m.p. 144~146° C. | 55 | " |
| 138 | 5-Cl-pyridin-2-yl-O-CH(C₂H₅)-CONH-CH₂-(2-bromophenyl) | m.p. 148~149° C. | 63 | " |
| 139 | 5-Cl-pyridin-2-yl-O-CH(C₂H₅)-CONH-CH₂-thienyl | m.p. 124~125° C. | 71 | " |
| 140 | 5-Br-pyridin-2-yl-O-CH(C₂H₅)-CONH-CH₂-phenyl | m.p. 145~148° C. | 47 | " |
| 141 | 5-Br-pyridin-2-yl-O-CH(C₂H₅)-CONH-CH₂-(2-methylphenyl) | m.p. 160~161° C. | 79 | " |

TABLE 1-continued

| Compound No. | Formula | Physical property | Yield (%) | State |
|---|---|---|---|---|
| 142 | 5-Br-pyridin-2-yl-OCH(C₂H₅)CONHCH₂-(2-Cl-C₆H₄) | m.p. 149~150° C. | 57 | " |
| 143 | 5-Br-pyridin-2-yl-OCH(C₂H₅)CONHCH₂-(2-thienyl) | m.p. 128~130° C. | 52 | " |
| 144 | 5-CF₃-pyridin-2-yl-OCH(C₂H₅)CONHCH₂-C₆H₅ | m.p. 107~108° C. | 48 | Colorless prism |
| 145 | 2,6-diCl-pyridin-4-yl-OCH(C₂H₅)CONHCH₂-C₆H₅ | m.p. 135~137° C. | 31 | Colorless needle |
| 146 | 6-Cl-2-CH₃-pyridin-4-yl-OCH(C₂H₅)CONHCH₂-C₆H₅ | m.p. 146~147° C. | 42 | " |
| 147 | 6-Cl-2-CH₃-pyridin-4-yl-OCH(C₂H₅)CONHCH₂-(2-CH₃-C₆H₄) | m.p. 169~171° C. | 57 | " |
| 148 | 6-Cl-2-CH₃-pyridin-4-yl-OCH(C₂H₅)CONHCH₂-(2-Cl-C₆H₄) | m.p. 160~163° C. | 81 | " |
| 149 | 6-Cl-2-CH₃-pyridin-4-yl-OCH(C₂H₅)CONHCH₂-(2-thienyl) | m.p. 115~117° C. | 24 | " |
| 150 | 5-Cl-pyridin-2-yl-OCH(n-C₃H₇)CONHCH₂-C₆H₅ | m.p. 147~148° C. | 67 | " |

TABLE 1-continued

| Compound No. | Formula | Physical property | Yield (%) | State |
|---|---|---|---|---|
| 151 | ![structure] CH₃-S(O)₂- pyrimidine with CH₃, C₂H₅, OCHCONHCH₂-(chlorophenyl) | m.p. 109~111° C. | 60 | " |
| 152 | ![structure] CF₃- pyrimidine with CH₃, C₂H₅, OCHCONHCH₂-phenyl | m.p. 107~108° C. | 35 | " |

As apparent from the following Examples, the pirimidinyloxyalkanamide derivative of the present invention exhibits superior activity on broad leaf weeds, which are difficult to be controlled, such as *Abutilon theophrasti, Sida spinosa, Cassia tora, Ipomoea purpurea*, to prior art phenoxyalkanoic acid amide derivatives, with notably improved efficiency when applied to cotton, soybean, etc. for summer cropping.

Namely, the pirimidinyloxyalkanamide derivative of the present invention is an excellent herbicide which can effectively control various kinds of paddy weeds such as *Echinochloa crusgalli, Scirpus hotarui*, etc., without giving any adverse effect of chemical on paddy-rice seedling, in paddy fields, and also a wide variety of grasses and broad leaf weeds including those which are difficult to be controlled, in various farmyards of wheat, cotton, soybean, sorghum, tomato, etc.

The pirimidinyloxyalkanamide derivative of the present invention may be synthesized according to the following reaction (A) or (B).

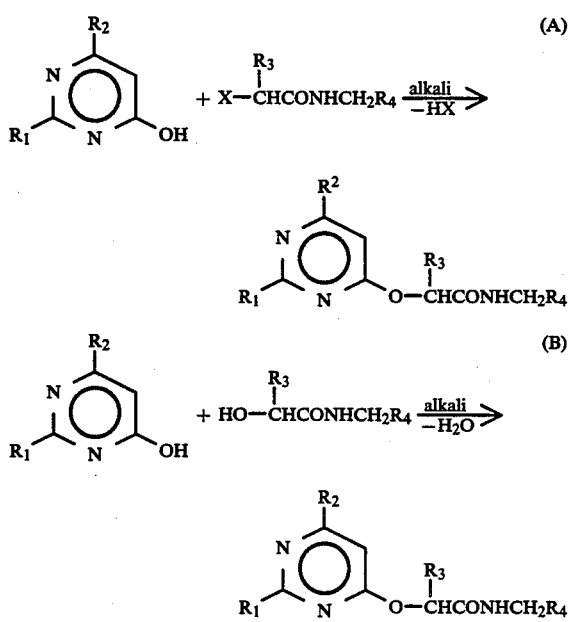

In the above formulae $R_1$, $R_2$, $R_3$ and $R_4$ have the same meanings as defined above, and X represents a chlorine atom or a bromine atom.

The above reactions may suitably be conducted in the presence of a suitable solvent with addition of a week alkali such as pyridine, triethylamine, sodium carbonate or potassium carbonate. The solvent to be used in the above reaction may include aromatic hydrocarbons such as benzene, toluene, xylene, etc., ethers such as tetrahydrofuran, dioxane, etc., ketones such as methyl ethyl ketone, dimethyl ketone, etc., and amides such as dimethylformamide, di-methylacetamide. Reaction temperature is not critical and may vary depending on the kinds of reagent and the solvent to be employed. However, reaction may preferably be conducted at a temperature ranging between 50° and 150° C. to be completed in about 1 to 10 hours.

Next, Synthesis Examples will be shown below.

SYNTHESIS EXAMPLE 1

Synthesis of N-(2-methylbenzyl)-2-(2,4-dimethyl-6-pyrimidi-nyloxy)butylamide (Compound No. 96)

To 50 ml of acetone were dissolved 2.6 g (0.021 mol) of 2,4-dimethyl-6-hydroxypyrimidine and 5.2 g (0.091 mol) of N-(2-methylbenzyl)-2-bromobutylamide, and then 3.5 g (0.025 mol) of anhydrous potassium carbonate powder was added thereto, followed by heating under reflux with stirring. The reaction solution was poured into water, and the product formed was extracted with ethyl acetate. The ethyl acetate layer was washed successively with dilute caustic soda and water and then dried over glauber's salt. Subsequently, the solvent was distilled off and the resulting crude crystal was recrystallized from ethanol to give N-(2-methyl-benzyl)-2-(2,4-dimethyl-6-pyrimidinyloxy)butylamide with m.p. 156° to 157° C. as a colorless needle crystal, at an yield of 58% relative to N-(2-methylbenzyl)-2-bromobutylamide.

SYNTHESIS EXAMPLE 2

Synthesis of N-(2-methylbenzyl)-2-(4-chloro-6-pyrimidinyloxy)-butylamide (Compound No. 135)

To 50 ml of acetone were dissolved 3.0 g (0.02 mol) of 4,6-dichloropyrimidine and 3.9 g (0.018 mol) of N-(2-methylbenzyl)-2-hydroxybutylamide, and then 3.0 g (0.022 mol) of anhydrous potassium carbonate powder was added thereto, followed by heating under reflux with stirring for 5 hours. The reaction solution was treated in the same manner as in Synthesis Example 1. The crude crystal obtained was recrystallized from ethanol to give 3.4 g of N-(2-methylbenzyl)-2-(4-chloro-6-pyrimidinyloxy)butylamide with m.p. 165° to 167° C. as a colorless needle crystal, at an yield of 57% relative to N-(2-methylbenzyl)-2-hydroxybutylamide.

SYNTHESIS EXAMPLE 3

Synthesis of N-benzyl-2-(4-bromo-6-pyrimidinyloxy)butylamide (Compound No. 140)

To 50 ml of acetone were dissolved 1.3 g (0.0055 mol) of 4,6-dibromopyrimidine and 1.3 g (0.0066 mol) of N-benzyl-2-hydroxybutylamide, and then 1.1 g (0.008 mol) of dry potassium carbonate powder was added thereto, followed by heating under reflux with stirring for 6 hours. The reaction solution was treated in the same manner as in Synthesis Example 1. The crude crystal obtained was recrystallized from ethanol to give 0.9 g of N-benzyl-2-(4-bromo-6-pyrimidinyloxy)butylamide with m.p. 145° to 146° C. as a colorless needle crystal, at an yield of 47% relative to 4,6-dibromopyrimidine.

Other compounds synthesized in the same manner as mentioned above are also listed in Table 1.

When the primidinyloxyalkanamide derivative of the present invention is used as a herbicide, it may be mixed with a carrier and, if necessary, with other auxiliaries and formed into any optional format of preparation to be usually used as a herbicide, such as dust, a fine granule, a granule, a wettable powder, an emulsifiable concentrate, a suspendable concentrate, a paste, a tablet, an aerosol, a fumigant, etc.

The above carrier may include inorganic materials such as kaolin, clay, talc, mica, diatomaceous earth, vermiculite, gypsum, calcium carbonate, dolomite, magnesium lime, apatite, zeolite, silicic anhydride, a synthetic calcium cilicate, etc.; plant materials such as wood powder, starch, cellulose, etc.; and, as liquid carrier, kerosine, mineral oils, toluene, xylene, ethylbenzene, cumene, methylnaphthalene, carbon tetrachloride, chloroform, dioxane, tetrahydrofuran, cyclohexane, isophorone, n-hexanol, cyclohexanol, ethylene glycol phenylether, dimethylformamide, etc.

One to several kinds of surfactants selected from the group consisting of nonionic, anionic, cationic and ampholytic ones may be admixed as an auxiliary for the purpose of emulsification, dispersion, wetting, spreading or stabilization of the active ingredient.

Further, a pesticide such as a fungicide, an insecticide and others or a fertilizer such as urea, ammonium sulfate, ammonium phosphate, a potassium salt and others or a soil improver may suitably be admixed for actual use. Also, a herbicide or other kind may suitably be incorporated.

The composition according to the present invention generally contains form 1 to 80% by weight of the derivative as an acitive ingredient based on the total amount of the herbicide composition, although it may differ depending on the format of preparations such as a dust, a granule, a wettable powder, an emulsifiable concentrate, a suspendable concentrate, etc.

The dose of the active ingredient to be applied, which may differ depending on the species of the target plant, may be generally from 1 to 30 g/a. More specifically, it may be from 1 to 20 g/a for paddy rice; from 1 to 30 g/a for soil treatment; and from 1 to 30 g/a for foliar treatment.

Next, Examples of the herbicides of the present invention will be illustrated. In the following Examples parts means parts by weight.

EXAMPLE 1

Herbicide composition comprising N-(2-chlorobenzyl)-2-(2-ethyltio-4-methyl-6-pyrimidinyloxy)-butylamide (Compound No. 32) as an active ingredient 8 Parts of the captioned compound, 30 parts of bentonite, 59 parts of talc, 1 part of Neopelex Powder (tradename, produced by Kao Atlas K.K.) and 2 parts of lignosulfonic acid soda were mixed homogeneously, and a small amount of water was added thereto, followed by kneading. The resulting mixture was granulated and dried to obtain a granule.

EXAMPLE 2

Herbicide composition comprising N-(2-chlorobenzyl)-2-(2-n-propyl-4-methyl-6-pyrimidinyloxy)-butylamide (Compound No. 99) as an active ingredient 50 Parts of the captioned compound, 48 parts of kaolin and 2 parts of Neopelex Powder were mixed homogeneously, followed by pulverization to obtain a wettable powder.

EXAMPLE 3

Herbicide composition comprising N-benzyl-2-(4-chloro-6-pyrimidinyloxy)butylamide (Compound No. 134) as an active ingredient 30 Parts of the captioned compound, 60 parts of xylene, 5 parts of dimethylformamide and 5 parts of Toxanon (tradename, produced by Sanyo Chemical Industries, Ltd.) were mixed homogeneously until the solid portions may completely be dissolved to obtain an emulsifiable concentrate.

EXAMPLE 4

Herbicide composition comprising N-(2-methylbenzyl)-2-(4-bromo-6-pyrimidinyloxy)-butylamide (Compound No. 141) as an active ingredient 5 Parts of the captioned compound, 50 parts of talc and 45 parts of kaolin were mixed homogeneously to obtain a powder.

TEST EXAMPLE 1

Test of treatment of paddy rice

Ube soil (alluvium clay loam) was charged in Wagner pots of 1/5000 are. Seeds of *Echinochloa crusgalli* delivered from dormance and tubers of slender spikerush (*Eleocharis acicularis*) were placed over the soil, and they were covered with soil lightly. Seeds of broad leaf weeds (*Rotala indica, Lindernia procumbens* and *Monochoria vaginalis*) and of *Scirpus juncoides* were then sown over the upper layer, and paddy-rice seedlings of 1.8 to 2 leaf stage were transplanted thereto, followed by addition of water to provide a flooded condition with a water depth of 3 cm. Subsequently, soil treatment was conducted with each agent (produced by using a wettable powder prepared according to Example 2 and diluting it with water such that the concentration of the active ingredient may be 1000 ppm) by pipetting it to the surface of the water so that the total amount of the active ingredient to be applied may be 20 g/a, respectively. The thus treated samples were kept in a glass chamber under control at an average temperature of 25° C. Exactly three weeks after treatment of the agents, herbicidal effect of each specimen compound was evaluated. The results are shown in Table 2.

TABLE 2

| Compound No. | A | B | C | D | E |
|---|---|---|---|---|---|
| 5 | 5 | 5 | 3 | 4 | 1 |
| 7 | 5 | 5 | 2 | 4 | 0 |
| 20 | 5 | 5 | 5 | 5 | 1 |
| 25 | 5 | 5 | 3 | 5 | 0 |
| 26 | 5 | 5 | 3 | 0 | 0 |
| 30 | 5 | 5 | 4 | 4 | 0 |
| 32 | 5 | 5 | 5 | 5 | 0 |
| 33 | 5 | 5 | 5 | 5 | 0 |
| 35 | 5 | 5 | 4 | 5 | 0 |
| 36 | 5 | 5 | 3 | 4 | 0 |
| 39 | 5 | 5 | 4 | 5 | 2 |
| 40 | 5 | 5 | 3 | 5 | 2 |
| 43 | 5 | 5 | 2 | 4 | 0 |
| 45 | 5 | 5 | 4 | 5 | 1 |
| 46 | 5 | 5 | 4 | 5 | 0 |
| 48 | 5 | 5 | 5 | 5 | 1 |
| 49 | 5 | 5 | 5 | 5 | 0 |
| 50 | 5 | 5 | 5 | 5 | 0 |
| 51 | 5 | 5 | 5 | 5 | 0 |
| 52 | 5 | 5 | 4 | 4 | 0 |
| 54 | 5 | 5 | 3 | 5 | 0 |
| 55 | 5 | 5 | 5 | 5 | 0 |
| 57 | 5 | 5 | 3 | 5 | 0 |
| 60 | 5 | 5 | 4 | 5 | 0 |
| 63 | 5 | 5 | 4 | 5 | 1 |
| 65 | 5 | 5 | 5 | 5 | 0 |
| 66 | 5 | 5 | 5 | 5 | 0 |
| 67 | 5 | 5 | 5 | 5 | 0 |
| 69 | 5 | 5 | 3 | 5 | 0 |
| 70 | 5 | 5 | 3 | 2 | 0 |
| 71 | 5 | 5 | 3 | 2 | 0 |
| 75 | 5 | 5 | 4 | 2 | 0 |
| 76 | 5 | 5 | 4 | 0 | 0 |
| 79 | 5 | 5 | 5 | 5 | 0 |
| 81 | 5 | 5 | 4 | 2 | 0 |
| 88 | 5 | 5 | 3 | 4 | 0 |
| 89 | 5 | 5 | 5 | 5 | 0 |
| 90 | 5 | 5 | 4 | 4 | 0 |
| 91 | 5 | 5 | 4 | 5 | 0 |
| 92 | 5 | 5 | 4 | 2 | 0 |
| 93 | 5 | 5 | 3 | 5 | 0 |
| 94 | 5 | 5 | 5 | 4 | 0 |
| 95 | 5 | 5 | 3 | 5 | 0 |
| 98 | 5 | 5 | 5 | 5 | 0 |
| 99 | 5 | 5 | 5 | 5 | 1 |
| 100 | 4 | 5 | 1 | 2 | 0 |
| 101 | 5 | 5 | 1 | 5 | 0 |
| 102 | 5 | 5 | 5 | 4 | 0 |
| 103 | 5 | 5 | 4 | 5 | 0 |
| 108 | 5 | 5 | 4 | 4 | 1 |
| 110 | 5 | 5 | 3 | 5 | 0 |
| 119 | 5 | 5 | 4 | 5 | 0 |
| 120 | 5 | 5 | 1 | 5 | 0 |
| 121 | 5 | 5 | 1 | 5 | 0 |
| 126 | 5 | 5 | 5 | 5 | 0 |
| 130 | 5 | 5 | 3 | 3 | 0 |
| 131 | 5 | 5 | 5 | 5 | 0 |
| 132 | 5 | 5 | 5 | 5 | 0 |
| 134 | 5 | 5 | 5 | 5 | 0 |
| 135 | 5 | 5 | 5 | 5 | 0 |
| 136 | 5 | 5 | 5 | 5 | 0 |
| 137 | 5 | 5 | 4 | 5 | 0 |
| 140 | 5 | 5 | 4 | 5 | 1 |
| 141 | 5 | 5 | 5 | 5 | 0 |
| 142 | 5 | 5 | 4 | 5 | 1 |
| 146 | 5 | 5 | 3 | 5 | 0 |
| 147 | 5 | 5 | 4 | 5 | 0 |

TABLE 2-continued

| Compound No. | A | B | C | D | E |
|---|---|---|---|---|---|
| 148 | 5 | 5 | 3 | 5 | 0 |

A: Echinochloa crusgalli
B: Broadleaf weeds (Rotala indica, Lindernia procumbens, Monochoria vaginalis)
C: Eleocharis acicularis
D: Scirpus juncoides
E: Paddy-rice seedling In Table 2, the herbicidal effects are shown according to the following judgement criteria.
5: Completely withered
4: Greatly damaged
3: Moderately damaged
2: Damaged a little
1: Slightly damaged
0: No damage (normal growth)

TEST EXAMPLE 2

Test of soil treatment

Ube soil (deluvium soil) was charged in Wagner pots of 1/5000 are, and seeds of the following plants were sown over it: Digitaria sanguinalis, Echinochloa crusgalli, Portulaca oleracea, Amaranthus retroflexus, Chenopodium album, wheat, cotton, soybean sorghum and tomato.

The seeds were covered with soil, and then soil treatment was conducted with each agent (produced by diluting, with water, a wettable powder prepared according to Example 2 such that the concentration of the active ingredient may be 1000 ppm.) by spraying it under pressure over the surface of the soil so that the total amount of the active ingredient to be applied may be 20 g/a, respectively. The thus treated samples were kept in a glass chamber under control at an average temperature of 25° C. Exactly three weeks after treatment of the agents, herbicidal effect of each specimen compound was evaluated. The results are shown in Table 3 and Table 4.

In Table 3, the herbicidal effects are shown according to the judgement criteria as defined in Test Example 1. In Table 4, compounds which are innoxious to each of the listed crops are given.

TABLE 3

| Compound No. | a | b | c | d | e | Compound No. | a | b | c | d | e |
|---|---|---|---|---|---|---|---|---|---|---|---|
| 1 | 1 | 4 | 5 | 5 | 5 | 70 | 4 | 5 | 5 | 5 | 4 |
| 3 | 5 | 5 | 5 | 5 | 5 | 71 | 3 | 5 | 5 | 5 | 3 |
| 4 | 5 | 5 | 5 | 5 | 5 | 75 | 4 | 5 | 5 | 5 | 4 |
| 11 | 5 | 5 | 5 | 5 | 5 | 76 | 3 | 5 | 5 | 5 | 5 |
| 12 | 5 | 5 | 5 | 5 | 5 | 77 | 4 | 5 | 5 | 5 | 3 |
| 13 | 4 | 5 | 5 | 5 | 5 | 78 | 5 | 5 | 5 | 5 | 4 |
| 14 | 5 | 5 | 5 | 5 | 5 | 79 | 4 | 5 | 5 | 5 | 4 |
| 20 | 5 | 5 | 5 | 5 | 5 | 89 | 3 | 5 | 5 | 3 | 5 |
| 22 | 5 | 5 | 5 | 5 | 5 | 90 | 2 | 5 | 5 | 3 | 5 |
| 25 | 5 | 5 | 5 | 5 | 5 | 96 | 5 | 5 | 5 | 5 | 5 |
| 27 | 5 | 5 | 5 | 5 | 5 | 97 | 4 | 5 | 5 | 5 | 5 |
| 28 | 5 | 5 | 5 | 5 | 5 | 98 | 5 | 5 | 5 | 5 | 5 |
| 30 | 4 | 5 | 5 | 2 | 0 | 99 | 5 | 5 | 5 | 5 | 5 |
| 32 | 5 | 5 | 5 | 5 | 5 | 100 | 4 | 5 | 5 | 5 | 5 |
| 33 | 4 | 5 | 5 | 5 | 5 | 101 | 4 | 5 | 5 | 5 | 4 |
| 35 | 3 | 5 | 5 | 5 | 5 | 102 | 4 | 5 | 5 | 5 | 4 |
| 36 | 5 | 5 | 5 | 5 | 5 | 104 | 5 | 5 | 5 | 5 | 5 |
| 37 | 2 | 5 | 5 | 5 | 5 | 106 | 4 | 5 | 5 | 5 | 5 |
| 38 | 5 | 5 | 5 | 5 | 5 | 108 | 2 | 4 | 5 | 5 | 5 |
| 39 | 4 | 5 | 5 | 5 | 5 | 110 | 4 | 5 | 5 | 5 | 5 |
| 41 | 3 | 5 | 5 | 4 | 5 | 112 | 5 | 5 | 5 | 5 | 5 |
| 42 | 3 | 5 | 4 | 5 | 5 | 113 | 5 | 5 | 5 | 5 | 5 |
| 43 | 5 | 5 | 5 | 5 | 5 | 114 | 3 | 5 | 5 | 4 | 4 |
| 46 | 5 | 5 | 5 | 5 | 5 | 115 | 5 | 5 | 5 | 5 | 5 |

TABLE 3-continued

| Compound No. | a | b | c | d | e | Compound No. | a | b | c | d | e |
|---|---|---|---|---|---|---|---|---|---|---|---|
| 47 | 5 | 5 | 5 | 5 | 5 | 120 | 2 | 5 | 5 | 5 | 5 |
| 48 | 2 | 5 | 5 | 5 | 5 | 121 | 5 | 5 | 5 | 5 | 4 |
| 49 | 2 | 3 | 5 | 5 | 5 | 123 | 2 | 5 | 4 | 4 | 5 |
| 50 | 2 | 5 | 5 | 5 | 5 | 131 | 5 | 5 | 5 | 5 | 5 |
| 51 | 4 | 5 | 5 | 5 | 5 | 132 | 5 | 5 | 5 | 5 | 5 |
| 52 | 2 | 5 | 5 | 5 | 5 | 133 | 3 | 5 | 5 | 5 | 4 |
| 53 | 5 | 5 | 5 | 5 | 5 | 134 | 5 | 5 | 5 | 5 | 5 |
| 54 | 3 | 5 | 5 | 5 | 5 | 135 | 5 | 5 | 5 | 5 | 5 |
| 55 | 5 | 5 | 5 | 5 | 5 | 136 | 2 | 3 | 5 | 4 | 4 |
| 56 | 4 | 4 | 5 | 5 | 5 | 137 | 5 | 5 | 5 | 5 | 5 |
| 57 | 3 | 5 | 5 | 5 | 5 | 138 | 4 | 5 | 5 | 5 | 4 |
| 58 | 2 | 5 | 5 | 4 | 3 | 139 | 4 | 5 | 5 | 5 | 5 |
| 59 | 3 | 5 | 5 | 5 | 5 | 140 | 5 | 5 | 5 | 5 | 5 |
| 60 | 5 | 5 | 5 | 5 | 5 | 141 | 3 | 5 | 5 | 5 | 5 |
| 61 | 5 | 5 | 5 | 5 | 5 | 143 | 4 | 5 | 5 | 5 | 5 |
| 63 | 4 | 5 | 5 | 5 | 3 | 146 | 1 | 5 | 5 | 5 | 5 |
| 64 | 5 | 5 | 5 | 5 | 5 | 147 | 4 | 5 | 5 | 5 | 5 |
| 65 | 3 | 5 | 5 | 5 | 5 | 148 | 3 | 5 | 5 | 5 | 4 |
| 66 | 4 | 5 | 5 | 4 | 5 | 149 | 5 | 5 | 5 | 5 | 5 |
| 67 | 3 | 5 | 5 | 4 | 4 | 150 | 1 | 5 | 5 | 5 | 5 |
| 68 | 4 | 5 | 5 | 5 | 5 | 152 | 5 | 5 | 5 | 5 | 5 |
| 69 | 4 | 5 | 5 | 5 | 4 | | | | | | | a: *Echinochloa crusgalli*
b: *Digitaria sanguinalis*
c: *Portulaca oleracea*
d: *Amaranthus retroflexus*
e: *Datura Stramonium*

TABLE 4

Compound innoxious to crops in dry-field soil treatment

| Crops | Compound No. |
|---|---|
| Wheat | 1, 11, 12, 13, 20, 30, 35, 36, 37, 38, 39, 41, 42, 43, 46, 47, 48, 49, 50, 51, 52, 53, 56, 57, 58, 59, 60, 61, 63, 64, 66, 68, 69, 70, 71, 75, 76, 77, 78, 79, 89, 90, 96, 97, 99, 100, 101, 102, 104, 106, 108, 110, 113, 114, 115, 120, 121, 122, 123, 131, 132, 133, 135, 136, 139, 141, 143, 146, 147, 148, 149, 150 |
| Cotton | 1, 4, 11, 12, 13, 20, 22, 27, 28, 30, 33, 35, 36, 37, 38, 39, 41, 42, 43, 46, 47, 48, 49, 50, 51, 52, 53, 54, 55, 56, 57, 58, 59, 60, 61, 63, 65, 66, 67, 68, 69, 70, 71, 75, 76, 77, 78, 79, 89, 90, 96, 97, 98, 99, 100, 101, 102, 104, 106, 108, 110, 112, 114, 115, 120, 122, 123, 131, 132, 133, 135, 136, |

TABLE 4-continued

Compound innoxious to crops in dry-field soil treatment

| Crops | Compound No. |
|---|---|
| Soybean | 139, 140, 141, 143, 146, 147, 148, 149, 150, 1, 4, 11, 12, 13, 14, 20, 22, 30, 32, 33, 35, 38, 39, 41, 42, 43, 46, 47, 48, 49, 50, 51, 52, 54, 56, 57, 58, 60, 61, 63, 64, 65, 66, 68, 69, 70, 71, 75, 76, 77, 78, 79, 89, 90, 97, 99, 101, 102, 106, 108, 114, 115, 120, 121, 122, 123, 133, 136, 146, 148 |
| Sorghum | 1, 13, 30, 35, 37, 38, 39, 41, 42, 48, 49, 50, 51, 52, 55, 56, 58, 59, 63, 65, 66, 67, 69, 71, 75, 76, 77, 78, 79, 89, 90, 100, 101, 102, 106, 108, 113, 114, 132, 133, 135, 136, 139, 141, 143, 146, 147, 149, 150 |
| Tomato | 25, 30, 38, 42, 47, 50, 51, 52, 53, 56, 58, 60, 61, 63, 64, 65, 66, 67, 68, 69, 75, 76, 77, 78, 79, 89, 150 |

TEST EXAMPLE 3

Test of soil treatment with a lower concentration of active ingredient

Ube soil (deluvium soil) was charged in Wagner pots of 1/5000 are, and tubers or seeds of the following plants were placed over it: hedge bindweed (*Convolvulus sepium*), *Ipomoea purpurea*, jimsonweed (*Datura stramonium*), bleaknightshade (*Solanum nigrum*, *Abutilon theophrasti*, *Sida spinosa*, *Cassia tora* and *Rumex cripus*.

The seeds and tubers were covered with soil, and then soil treatment was conducted with each agent (produced by using a wettable powder prepared according to Example 2 and diluting it with water such that the concentration of the active ingredient may be 1000 ppm) by spraying it under pressure over the surface of the soil so that the total amount of the active ingredient to be applied may be 20 g/a, 10.5 g/a or 2.5 g/a, respectively. The thus treated samples were kept in a glass chamber under control at an average temperature of 25° C. Exactly three weeks after treatment of the agents, herbicidal effect of each specimen compound was evaluated. The results are shown in Table 5.

TABLE 5

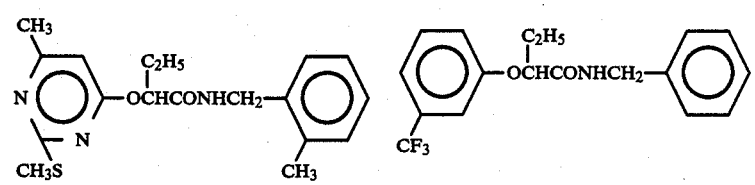

Compounds

Compound No. 4

Compound disclosed in Japanese Unexamined Patent Publication No. 26945/1984
Compound No. 1

| | rate g/a | | | | | | | |
|---|---|---|---|---|---|---|---|---|
| Species | 20 | 10 | 5 | 2.5 | 20 | 10 | 5 | 2.5 |
| *Convolvulus sepium* | 3 | 2 | 1 | 0 | 2 | 1 | 1 | 0 |
| *Ipomoea purpurea* | 5 | 4 | 4 | 2 | 2 | 1 | 1 | 0 |
| *Datura stramonium* | 5 | 3 | 2 | 1 | 3 | 2 | 1 | 0 |
| *Solanum nigrum* | 5 | 4 | 3 | 2 | 4 | 3 | 2 | 1 |
| *Abutilon theophrasti* | 5 | 5 | 4 | 1 | 1 | 0 | 0 | 0 |
| *Sida spinosa* | 5 | 5 | 5 | 4 | 1 | 0 | 0 | 0 |
| *Cassia tora* | 5 | 4 | 3 | 3 | 2 | 1 | 1 | 0 |
| *Rumex cripus* | 5 | 5 | 4 | 3 | 4 | 4 | 3 | 2 |

In Table 5, the herbicidal effects are shown according to the judgement criteria as defined in Test Example 1.

TEST EXAMPLE 4

Test of foliar treatment

Ube soil (deluvium soil) was charaged in Wagner pots of 1/5000 are, and the following plants were grown thereon: *Digitaria sanguinalis, Echinochloa crusgalli, Portulaca oleracea, Amaranthus retroflexus, Chenopodium album* and wheat.

An agent was prepaed by using a wettable powder obtained from each specimen compound and diluting it with a water containing 100 ppm of Neostelin (tradename, produced by Kumiai Kagaku K.K.), as a wetter, such that the concentration of the active ingredient may be 0.2% by weight. The stem and leaf portions of the above plants were uniformly treated with the thus prepared agent by spraying them under pressure so that the total amount to be applied may be 5 ml per pot. The thus treated samples were kept in a glass chamber under control at an average temperature of 25° C. Exactly three weeks after treatment of the agents, herbicidal effect of each specimen compound was evaluated. The results are shown in Table 6.

TABLE 6

| Compound No. | a | b | c | d | e | f |
|---|---|---|---|---|---|---|
| 4 | 3 | 3 | 4 | 4 | 4 | 1 |
| 10 | 2 | 4 | 4 | 4 | 4 | 2 |
| 14 | 5 | 5 | 4 | 4 | 5 | 1 |
| 22 | 2 | 4 | 5 | 4 | 5 | 2 |
| 27 | 3 | 4 | 5 | 4 | 4 | 2 |
| 32 | 5 | 3 | 4 | 4 | 5 | 1 |
| 38 | 4 | 4 | 4 | 4 | 3 | 0 |
| 45 | 3 | 4 | 5 | 4 | 4 | 2 |
| 77 | 2 | 2 | 5 | 4 | 5 | 1 |
| 78 | 3 | 2 | 4 | 4 | 5 | 1 |
| 98 | 4 | 4 | 5 | 4 | 5 | 1 |
| 103 | 3 | 5 | 5 | 2 | 5 | 1 |
| 104 | 4 | 4 | 5 | 4 | 5 | 3 |
| 120 | 4 | 4 | 5 | 4 | 5 | 1 |
| 121 | 0 | 4 | 5 | 4 | 5 | 0 |
| 132 | 2 | 5 | 5 | 5 | 5 | 1 |
| 138 | 1 | 3 | 4 | 4 | 4 | 3 |
| 140 | 4 | 5 | 5 | 5 | 5 | 0 | a: *Echinochloa crusgalli*
b: *Digitaria sanguinalis*
c: *Portulaca oleracea*
d: *Amaranthus retroflexus*
e: *Datura stramonium*
f: *Triticum aestivum*

In Table 6, the herbicidal effects are shown according to the judgement criteria as defined in Test Example 1.

We claim:

1. A pyrimidinyloxyalkanamide derivative of Formula 1:

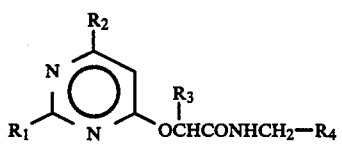

(1)

wherein $R_1$ represents a hydrogen atom, a halogen atom, a lower alkyl group, a lower alkylthio group, a lower alkenylthio group, a lower alkynylthio group, a halogenated lower alkenylthio group, a cycloalkylthio group, a phenoxyalkylthio group, a lower alkoxyl group, an amino group, a methanesulfonyl group, a trifluoromethyl group, an anilino group which may be substituted with a halogen atom or a benzylthio group which may be substituted with a halogen atom; $R_2$ represents a hydrogen atom, a halogen atom, a lower alkyl group, a trifluoromethyl group, an amino group, a lower alkoxyl group or a lower alkylthio group; $R_3$ represents an ethyl group or an n-propyl group; and $R_4$ represents a cyclohexyl group, a thienyl group, a pyridyl group, a furyl group or a

group wherein X and Y may be the same or different and each represent a hydrogen atom, a lower alkyl group, a trifluoromethyl group, a lower alkoxyl group or a halogen atom.

2. The derivative according to claim 1, wherein $R_1$ represents H, $CH_3S-$,

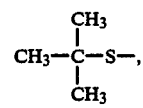

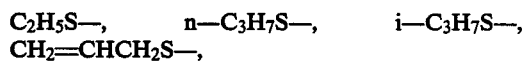

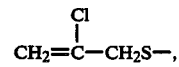

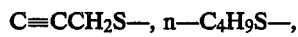

$C\equiv CCH_2S-$, $n-C_4H_9S-$,

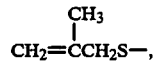

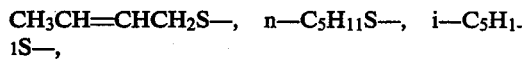

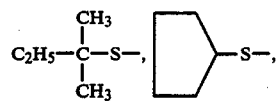

$CH_3-$, $n-C_3H_7-$, $i-C_3H_7-$, or $n-C_4H_9-$,
$R_2$ represents $CH_3-$, $Cl-$, $t-C_4H_9-S-$, $n-C_3H_7-$, $F_3C-$, $Cl-$ or
$R_3$ represents $-C_2H_5$ and
$R_4$ represents

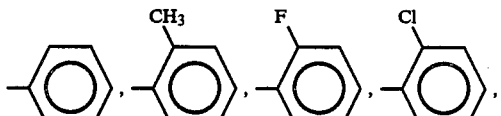

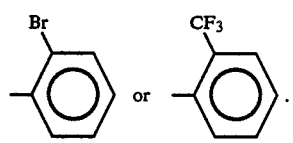

3. The derivative according to claim 1, wherein the derivative is one selected from the group consisting of

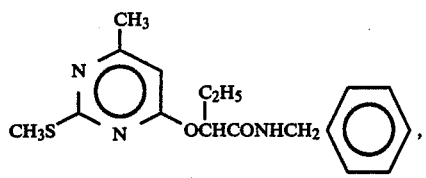,

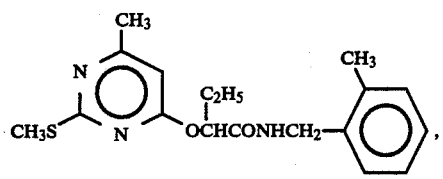,

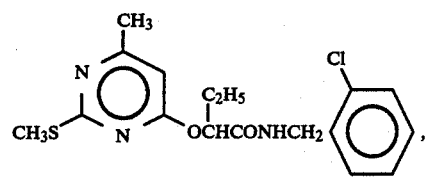,

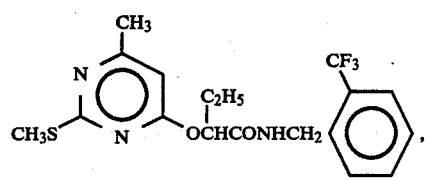,

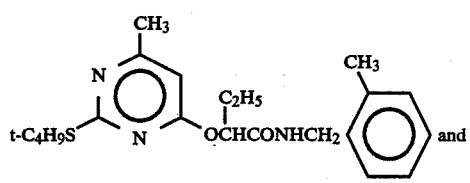 and

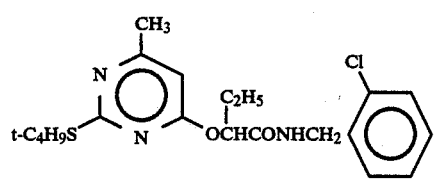.

4. The derivative according to claim 3 which is

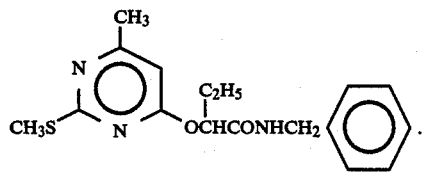.

5. The derivative according to claim 3 which is

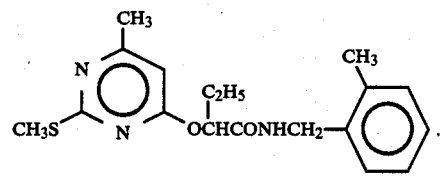.

6. The derivative according to claim 3 which is

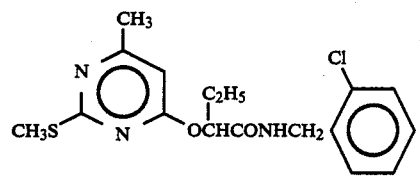.

7. The derivative according to claim 3 which is

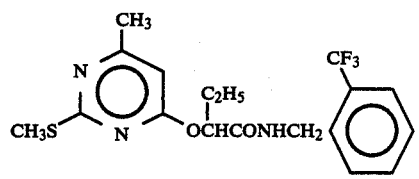.

8. The derivative according to claim 3 which is

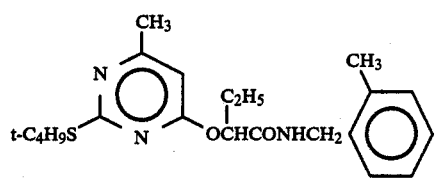.

9. The derivative according to claim 3 which is

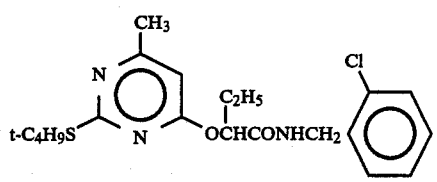.

10. A herbicide composition comprising, as an active ingredient, a pirimidinyloxyalkanamide derivative of Formula 1:

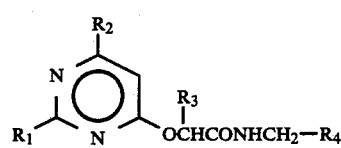 (1)

wherein $R_1$ represents a hydrogen atom, a halogen atom, a lower alkyl group, a lower alkylthio group, a lower alkenylthio group, a lower alkynylthio group, a halogenated lower alkenylthio group, a cycloalkylthio group, a phenoxyalkylthio group, a lower alkoxyl group, an amino group, a methanesulfonyl group, a trifluoromethyl group, an anilino group which may be substituted with a halogen atom or a benzylthio group which may be substituted with a halogen atom; $R_2$ represents a hydrogen atom, a halogen atom, a lower alkyl group, a trifluoromethyl group, an amino group, a lower alkoxyl group or a lower alkylthio group; $R_3$ represents an ethyl group or an n-propyl group; and $R_4$ represents a cyclohexyl group, a thienyl group, a pyridyl group, a furyl group or a

group wherein X and Y may be the same or different and each represent a hydrogen atom, a lower alkyl group, a trifluoromethyl group, a lower alkoxyl group or a halogen atom,
said active ingredient being in an amount of from 1 to 80% by weight based on the total weight of the herbicidal composition with the remainder of said herbicidal composition being at least one auxiliary component.

11. The herbicide composition according to claim 10, wherein $R_1$ represents H, $CH_3S-$,

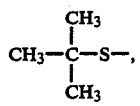

$C_2H_5S-$, $n-C_3H_7S-$, $i-C_3H_7S-$, $CH_2=CHCH_2S-$,

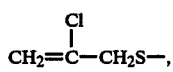

$C\equiv CCH_2S-$, $n-C_4H_9S-$,

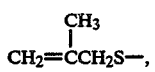

$CH_3CH=CHCH_2S-$, $n-C_5H_{11}S-$, $i-C_5H_{11}S-$,

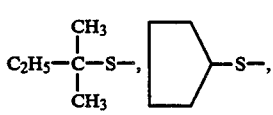

$CH_3-$, $n-C_3H_7-$, $i-C_3H_7-$, or $n-C_4H_9-$,
$R_2$ represents $CH_3-$, $Cl-$, $t-C_4H_9-S-$, $n-C_3H_7-$, $F_3C-$, $Cl-$ or $Br-$,
$R_3$ represents $-C_2H_5$ and
$R_4$ represents

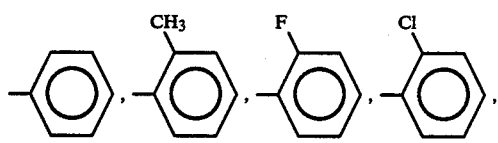

-continued

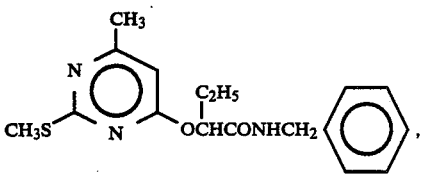

12. The herbicide composition according to claim 10, wherein the derivative is one selected from the group consisting of

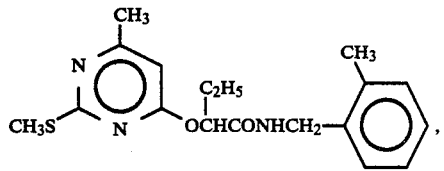

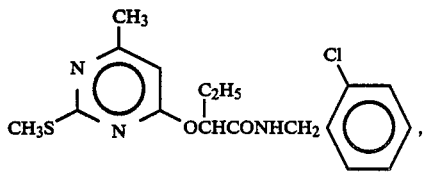

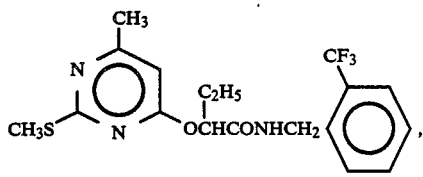

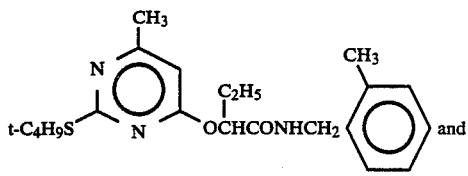

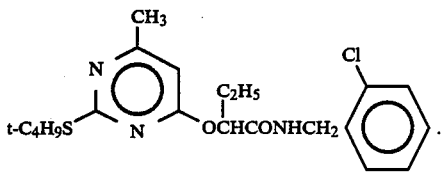

and

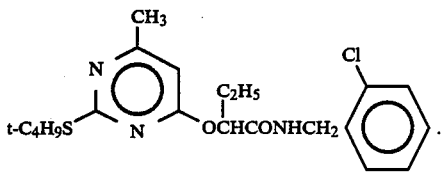

13. The herbicide composition according to claim 10, which contain an agriculturally acceptable carrier.

* * * * *